United States Patent [19]

Hönel et al.

[11] 4,223,141

[45] Sep. 16, 1980

[54] PREPARATION OF METHOXY-METHYL MELAMINES

[75] Inventors: Hans Hönel; Karlfried Keller; Walter Michel, all of Frankfurt am Main; Manfred Schön, Rodgau, all of Fed. Rep. of Germany

[73] Assignee: Cassella Aktiengesellschaft, Frankfurt am Main, Fed. Rep. of Germany

[21] Appl. No.: 51,851

[22] Filed: Jun. 25, 1979

[30] Foreign Application Priority Data

Sep. 13, 1978 [DE] Fed. Rep. of Germany ....... 2839713

[51] Int. Cl.² ........................................... C07D 251/64
[52] U.S. Cl. .................................................. 544/196
[58] Field of Search .......................................... 544/196

[56] References Cited

U.S. PATENT DOCUMENTS

| 2,645,625 | 7/1953 | Bonzagni | 544/196 |
| 2,998,410 | 8/1961 | Jefts et al. | 260/67.6 |
| 3,824,232 | 7/1974 | Pusch et al. | 544/196 |

FOREIGN PATENT DOCUMENTS

| 2716006 | 10/1978 | Fed. Rep. of Germany | 544/196 |
| 1086826 | 8/1954 | France . | |
| 432839 | 9/1967 | Switzerland . | |
| 611013 | 10/1948 | United Kingdom . | |
| 971587 | 9/1964 | United Kingdom . | |

*Primary Examiner*—John M. Ford
*Attorney, Agent, or Firm*—Connolly and Hutz

[57] ABSTRACT

This invention relates to a process for the manufacture of methanol-etherified methylolmelamines which are largely monomeric containing more than 5 mols of formaldehyde and more than 4 mols of methyl-etherified methylol groups, per mol of melamine, and having a viscosity of less than 20 pascal-seconds at 25° C. and a solids content of at least 95%, comprising (a) methylolating melamine with formaldehyde at a molar melamine:formaldehyde ratio of 1:6.5 to 1:8 for 1½ to 5 hours at 50° C. to 85° C., with the formaldehyde source being an aqueous solution of formalin containing 30 to 50% by weight of formaldehyde and having a pH of 6.7 to 7.3, and (b) etherifying the resulting suspension of methylolmelamine with 15 to 30 mols of methanol per mol of melamine at temperatures of 30° C. to 60° C. in the presence of a strong acid.

10 Claims, No Drawings

PREPARATION OF METHOXY-METHYL MELAMINES

The invention relates to a process for the manufacture of methyl-etherified methylolmelamines which are largely monomeric and which contain, per mol of melamine, more than 5 mols of formaldehyde and more than 4 mols of methyl-etherified methylol groups and which, at a solids content of at least 95% by weight, have a viscosity of less than 20 Pa.s (Pa.s=Pascal seconds; the SI unit of dynamic viscosity) at 25° C.

Melamine resins of this type are used, for example, as so-called high-solids lacquer resins for the manufacture of paints, lacquers and varnishes. Because of their low viscosity, while having, at the same time, relatively high solids contents, the lacquers and varnishes need only contain a small quantity of volatile solvents for processing conditions. As a result, when the lacquers and varnishes are processed, for example when sprayed-on stoving lacquers and varnishes are stoved, only small quantities of volatile organic solvents are liberated, which is very desirable for the preservation of the environment.

According to Example 1 of British Pat. No. 1,030,268, it is possible to prepare melamine resins of this type by methylolating melamine using 11 mols of paraformaldehyde per mol of melamine in methanolic solution in the presence of a basic catalyst and by subsequently etherifiying the product twice with excess methanol in the presence of a strong inorganic acid. Since not more than 6 mols of formaldehyde become attached, per mol of melamine, either the effluent and the exit gases become greatly polluted by the formaldehyde which is present in excess, or the formaldehyde which is present in excess must be worked up at additional expense. If 6.5-8 mols of paraformaldehyde per mol of melamine are employed in this process instead of 11 mols of paraformaldehyde, products are obtained, which have a higher viscosity as a result of a higher degree of condensation and a lower degree of etherification and which have a viscosity higher than 1,000 Pa.s at a solids content of 95% by weight. In addition, the melamine resins thus prepared only have a low stability as well as reduced compatibility with hydrophobic components and, as a result, are not very suitable as so-called high-solids lacquer resins.

U.S. Pat. No. 2,918,452 describes a process for the manufacture of methyl-etherified melamine resins which are largely monomeric, wherein melamine is first methylolated at a pH value of 8 to 13 with paraformaldehyde in a molar ratio of 1:6.5 to 20, in a suspension of a hydrocarbon, such as xylene, and in the presence of 8 to 20% of water. The methylolation product solidifies to give a solid mass, which is ground and affords a suspension of the methylolmelamine in the hydrocarbon. The subsequent acid etherification with excess methanol can be carried out in the presence of the hydrocarbon or after it has been removed. Besides the use of paraformaldehyde, which is obtained by concentrating aqueous formaldehyde solutions in a manner requiring a considerable technical effort, disadvantages of this process which should be mentioned are, in particular, the comminution of the crystalline methylolmelamine which is produced as the intermediate product and the use of the hydrocarbon, which causes a fire hazard and which pollutes the environment, while its use also reduces the space-time yield.

In Example 1 of U.S. Pat. No. 3,020,255, a methyl-etherified methylolmelamine is manufactured by mixing melamine with 6.18 mols of 37% strength aqueous formaldehyde and adjusting the pH value of the system to 7.2 to 7.8 with triethylamine. The mixture is heated to 90° C. in the course of 10 minutes and is then allowed to cool. The precipitate thus obtained is dehydrated to a water content of 6% at 40° to 50° C., in vacuo, and is then etherified with 4.7 mols of methanol under acid conditions for 10 minutes at room temperature. The disadvantage is the dehydration required, in the course of which the product ceases to be stirrable. In addition, unless repeated recrystallisations are carried out, only highly viscous methyl-etherified methylolmelamines are obtained as the end products.

In the process disclosed in U.S. Pat. No. 2,998,410, the highly methylolated melamine which is first prepared must be isolated and dried to water contents of less than 20% before it can be etherified in a subsequent stage. Moreover, additional water must be added to the methylolmelamine after the methylolation, to enable it to be isolated in conventional apparatus. The process is not advantageous from the cost point of view and its space-time yield is poor.

In the process of U.S. Pat. No. 2,998,411, the pH value is increased to 8 to 11 during the methylolation by continuously adding a basic catalyst. The resulting methylolmelamine must be isolated and, if it is to be etherified in a single stage, must be dried. Unless the methylolmelamine is dried, it is necessary to carry out a two-stage etherification, the use of an entraining agent, such as xylene or toluene, normally being required in the first etherification stage.

In the process, disclosed in British Pat. No. 674,948, for the manufacture of methyl-etherified methylolmelamines which are largely monomeric, melamine is methylolated with 6 to 9 mols of aqueous formaldehyde at 50° to 80° C. in as short a time as possible, for example 40 minutes, and the reaction batch is then etherified with methanol in the presence of a strong acid, without isolating the methylolmelamine. However, the melamine resins manufactured in accordance with this process are highly viscous at 25° C. and at a solids content of 95% by weight and have a viscosity higher than 1,000 Pa.s.

The processes disclosed hitherto for the manufacture of methyl-etherified methylolmelamines which are largely monomeric either require an involved intermediate isolation, or at least partial dehydration, of the methylolmelamine, or, if they are carried out without intermediate isolation of the methylolmelamine, only afford highly viscous methyl-etherified methylolmelamines. The difficulties of the previous processes are due to the fact that the highly methylolated melamine produced in the methylolation makes the batch more and more difficult to stir, so that it becomes necessary to dilute the suspension and subsequently to isolate the methylolmelamine. If complete methylolation is forgone, in order to obtain a batch which can still be stirred, the end products obtained are highly viscous methyl-etherified methylolmelamines, because the free amino groups of the incompletely methylolated methylolmelamines undergo a preferential condensation reaction with methylol groups to form high-molecular resinous components with a correspondingly high viscosity.

A process for the manufacture of low-viscosity methyletherified methylolmelamines which are largely monomeric has also already been suggested (German patent application No. 2,716,006), in which melamine and formaldehyde are reacted in a molar ratio of 1:6.2 to 1:8 in the presence of a basic catalyst in a reaction mixture containing 10 to 40% by weight of water and 40 to 20% by weight of methanol, at temperatures of 40° to 60° C., to give a suspension of methylolmelamine and this is then etherified in the presence of a total of 15 to 30 mols of methanol per mol of melamine, at temperatures of 25° to 50° C., in the presence of a strong acid. Problems of removing the heat of reaction can occur in this process, with fairly large batches, owing to the relatively low temperature in the methylolation reaction.

The invention was thereby based on the object of avoiding the disadvantages in the previous processes for the manufacture of methyl-etherified methylolmelamines which are largely monomeric and contain more than 5 mols of formaldehyde and more than 4 mols of methyl-etherified methylol groups, per mol of melamine, and which have a viscosity of less than 20 Pa.s at 25° C. and at a solids content of at least 95% by weight. It was the particular purpose of the process according to the invention to obtain, in the methylolation reaction, a suspension of highly methylolated methylolmelamines which is readily stirrable and which can be etherified immediately afterwards in the same vessel, in a single stage, without isolating or drying the methylolmelamines and without the use of an entraining agent.

In accordance with the invention, this object is achieved by methylolating melamine for 1½ to 5 hours at 50° to 85° C. in a molar ratio of 1:6.5 to 1:8 with an aqueous formalin solution which contains between 30 and 50% by weight of formaldehyde and which has been adjusted to pH values between 6.7 and 7.3, and etherifying the resulting, readily stirrable suspension of the methylolmelamine with 15 to 30 mols of methanol per mol of melamine at temperatures of 30° to 60° C. in the presence of a strong acid.

The process according to the invention is particularly suitable for the manufacture of methyl-etherified methylolmelamines which are largely monomeric and which contain more than 5.5 mols of formaldehyde and 4.3 to 5.1 mols of methyl-etherified methylol groups, per mol of melamine.

In the process according to the invention, formaldehyde is employed in the form of the customary aqueous formalin solutions which contain between 30 and 50% by weight of formaldehyde and which can contain up to 12% by weight of methanol as a stabiliser. The lower the methanol content of the formalin solution, the lower is the viscosity of the end products normally obtained. If appropriate, it is also possible to use mixtures of aqueous solutions containing a low percentage of formaldehyde and paraformaldehyde. 6.5 to 8 mols, preferably 7 to 7.5 mols, of formaldehyde must be present per mole of melamine. Formaldehyde solutions containing more than 50% by weight of formaldehyde are only employed for special applications because of their low stability. The methylolmelamines manufactured with these solutions in accordance with the process according to the invention tend to form crusts on the walls of the vessel, particularly in the case of fairly large batches, owing to the lack of water as a diluent.

In accordance with the invention, the aqueous formalin solution is adjusted to pH values between 6.7 and 7.3 before being combined with the melamine. For this adjustment of the pH it is possible to use organic and/or inorganic compounds with a basic reaction, such as, for example, alkali metal hydroxides, such as sodium or potassium hydroxide, alkali metal carbonates or alkali metal bicarbonates, such as, for example, sodium or potassium carbonate, sodium or potassium bicarbonate, secondary alkali metal phosphates, such as, for example, disodium hydrogen phosphate, alkali metal borates or organic amines, such as trialkylamines, for example triethylamine, tripropylamine and tributylamine. It is preferable to use borax for adjusting the pH of the formaldehyde solution, because suspensions of highly methylolated methylolmelamines which have a particularly low viscosity and are thus particularly easy to stir are then obtained.

Normally, 0.01 to 1% by weight of the compound with a basic reaction, relative to the weight of formaldehyde present in the formaldehyde solution, is required in order to adjust the pH value of the formaldehyde solution to values between 6.7 and 7.3. The quantity of basic compound required is, of course, dependent on the acid content of the formaldehyde solution. The formaldehyde solution used should contain as little formicacid as possible, as a rule less than 0.1% by weight of formic acid. Formaldehyde solutions containing less than 0.01% by weight of formic acid (the formalin solution then exhibits a pH value between 3.4 and 3.5) give particularly good results. It is also possible to use a mixture of different substances with a basic reaction for adjusting the pH value. The aqueous formaldehyde solution which has been adjusted to pH values between 6.7 and 7.3 is mixed with the melamine in a 1:(6.5 to 8) molar ratio of melamine:formaldehyde and is warmed to a temperature of 50° to 80° C., while stirring, in the course of which the melamine dissolves.

The methylolation is carried out at temperatures of 50° to 85° C., preferably 65° to 75° C., for 5 to 1½ hours, preferably 3 to 2 hours, the reaction batch being stirred. Since the methylolation requires a fairly long reaction time at low temperatures and, conversely, the desired degree of methylolation is achieved after only a fairly short time at high reaction temperatures, the end point of the methylolation must be determined by preliminary tests. In this it can be assumed that, for the same molar ratios of melamine to formaldehyde, the viscosity of the methyl-etherified methylolmelamines which are largely monomeric will be reduced if the viscosity of the aqueous suspension of methylolmelamines increases. Since the aqueous suspension of methylolmelamines gradually becomes more viscous during the course of the methylolation, the end point of the methylolation must be chosen in such a way that the methylolmelamine is produced without the formation of rims or crusts and dissolves completely during the etherification.

For stirring the reation batch it is appropriate to use a near-edge stirrer, that is to say a stirrer of a type which, in addition, stirs close to the entire wall, covered with liquid, of the container, since this avoids the formation of crusts on the container wall. Once crusts of this type have been formed, they can subsequently only be etherified with methanol with difficulty, or not at all. Examples of suitable stirrers are anchor and hook stirrers, the shape of which has been adjusted to the shape of the container.

A readily stirrable suspension of highly methylolated melamine, which can subsequently be etherified with methanol in the same reaction vessel, without the necessity of isolating the methylolmelamine or carrying out intermediate drying, is obtained by the process according to the invention.

Etherification is carried out by adding methanol to the resulting suspension in such a quantity that a total of 15 to 30 mols of methanol is present per mol of melamine. The etherification is carried out with stirring, at temperatures of 30° to 60° C., preferably 35° to 45° C., in the presence of 0.5 to 10% by weight, preferably 1 to 5% by weight, of a strong acid, relative to the weight of the starting components melamine and formaldehyde. If the etherification with methanol is carried out at a lower temperature than the methylolation, it is appropriate not to cool the suspension of the methylolmelamine to the etherification temperature until after the methanol has been added, since this ensures that the batch remains stirrable even under less favourable circumstances.

Suitable strong acids can be mineral acids, such as, for example, sulphuric acid, hydrochloric acid, phosphoric acid, carboxylic acids, such as, for example, trichloroacetic acid, or sulphonic acids, such as, for example, p-toluenesulphonic acid. Mixtures of strong acids can also be used. It is advantageous to use nitric acid. THe etherification is complete after 20 minutes to a maximum of 3 hours, depending on the reaction conditions. A clear solution is formed when the etherification is complete.

Finally, the batch is worked up in a known manner, that is to say, for example, with sodium or potassium carbonate, sodium or potassium hydroxide, and is neutralised or rendered weakly alkaline and the excess methanol is distilled off under reduced pressure, together with the water present in the batch. After the volatile constituents have been completely removed, the melamine resin is filtered, for example through kieselguhr, in order to remove salts.

The largely monomeric, methyl-etherified methylolmelamines which are produced by the process according to the invention have a viscosity of less than 20 Pa.s at 25° C. and at a solids content of at least 95% by weight. Low viscosity melamine resins of this type are, however, only obtained if at least 6.5 mols of formaldehyde, the pH value of which has been adjusted to 6.7 to 7.3, are employed per mol of melamine. If less than 6.5 mols of formaldehyde are employed per mol of melamine, the methylolmelamines which are formed tend to form rims and crusts and, in addition, produce more highly viscous melamine resins as a result of the condensation of the incompletely methylolated intermediate products. Low-viscosity methyletherified methylolmelamines, which cause particularly little environmental pollution and only a slight pollution of effluent and exit gases, are formed as a melamine:formaldehyde molar ratio of 1:(7 to 7.5). The use of more than 8 mols of formaldehyde per mol of melamine gives products which, compared with the products manufactured within the molar ratios claimed, do not exhibit improved properties, but which pollute the environment as a result of the unnecessarily large quantity of formaldehyde. In addition, the higher water content makes the subsequent etherification more difficult.

If the aqueous formaldehyde solution is adjusted to pH values below 6.7 before the addition of the melamine, methylolmelamines of higher molecular weight are formed, as the result of a condensation reaction, and these produce more highly viscous methyl-etherified methylolmelamines, after the etherification; if the pH value of the formaldehyde solution is above 7.3, highly viscous, clotted methylolmelamines which are difficult to stir and can only be partially etherified because of the formation of rims and crusts, are formed after a short time. Carrying out the methylolation below 50° takes a very long time and gives a viscous suspension of methylolmelamine which can only be stirred with difficulty or not at all. Although methylolation above 85° C. gives a methylolmelamine suspension of low viscosity, this produces only viscous end products in the subsequent etherification. After the melamine has been added to the formaldehyde solution, the pH value of the reaction batch changes. It is not necessary, in the process according to the invention, to follow or to adjust the pH value which changes during the methylolation.

The methylolmelamines which are produced as an intermediate product in the process according to the invention, and the methyl-etherified methylolmelamines, are mixtures of different chemical species, as is customary in the chemistry of melamine resins. The composition quoted in a particular case represents the average composition of the mixture.

The process according to the invention constitutes a simple, one-pot process which causes little environmental pollution and is economical for producing low-viscosity methyletherified methylolmelamines which are largely monomeric, without employing a large excess of formaldehyde, without adding an inert solvent and with a single-stage etherification reaction, without isolating and intermediately drying methylolmelamines containing water and without the use of an entraining agent.

The products obtained by the process according to the invention can be used, for example, for finishing textiles and paper and, in combination with alkyd resins, oil-free polyesters or acrylic resins, for the high-solids sector of lacquering to order to produce high-gloss, scratch-resistant coatings which have very good resistance to weathering, and also as adhesives. If the addition of solvents is necessary in the particular application, only small quantities need be added, owing to the low viscosity of the products.

The examples which follow serve to illustrate the invention further. Percentages represent percentages by weight.

EXAMPLE 1

Melamine:formaldehyde:methanol molar ratio = 1:7.4:25

1,139 g of a 39 % strength aqueous formaldehyde solution (pH 3.5) are adjusted to pH 7 in a 4-liter three-necked flask by adding 1 g of borax ($Na_2B_4O_7.10H_2O$). After adding 252 g of melamine, a clear solution is formed on warming the batch to 65° C., while stirring with a hook stirrer. Methylolation is then carried out for 2½ hours at 65°, a readily stirrable slurry being formed. After 1,600 g of methanol have been added, the contents of the flask are cooled to 40° C. in the course of 1 hour and 27 g of 55% strength nitric acid are added for the etherification. With the heating switched off and cooling applied, a clear solution is formed after approx. 1 hour and this is immediately adjusted to pH 8.5 with sodium hydroxide solution and concentrated under a waterpump vacuum until an internal temperature of 85° C. is reached.

Filtration through kieselguhr gives a 95% strength methyl-etherified methylolmelamine (the solids content is calculated from the loss in weight undergone by 2 g of the product when heated to 120° C. for one hour in an aluminium dish), which has a viscosity of 5.1 Pa.s at 25°

C. and which contains approx. 5.8 mols of formaldehyde and approx. 4.9 mols of methyl-etherified methylol groups, per mol of melamine.

If the formaldehyde used for the methylolation is adjusted to pH 7 with 0.12 g of sodium hydroxide instead of 1 g of borax, a methyl-etherified methylolmelamine, of the same composition is formed, which has a viscosity of 6.7 Pa.s at a solids content of 95%.

If the methylolation in the above example is carried out with a formaldehyde which has been adjusted to pH 7 with 0.44 g of potassium carbonate instead of 1 g of borax, a methyl-etherified methylolmelamine, of the same composition, which has a viscosity of 5.9 Pa.s at a solids content of 95%, is obtained after working up.

If the methylolation in accordance with Example 1 is carried out with a formaldehyde which has been adjusted to pH 7 with 0.58 g of sodium bicarbonate instead of 1 g of borax, a methyl-etherified methylolmelamine, of the same composition, which has a viscosity of 4.4 Pa.s at a solids content of 95%, is formed after etherification.

EXAMPLE 2

Melamine:formaldehyde:methanol molar ratio = 1:7.4:21

1,344 g of methanol are added at 65° C. to the aqueous suspension of methylolmelamine obtained in accordance with Example 1 and, after cooling to 40° C., as described in that example, etherification is carried out in the presence of 27 g of 55% strength nitric acid and the mixture is further processed.

The resulting 95% strength methyl-etherified methylolmelamine, has a viscosity of 9.3 Pa.s at 25° C. and contains approx. 5.7 mols of formaldehyde and approx. 4.6 mols of methyl-etherified methylol groups, per mol of melamine.

EXAMPLE 3

Melamine:formaldehyde:methanol molar ratio = 1:6.8:25

1,046 g of a 39% strength aqueous solution of formaldehyde (pH 3.7) are adjusted to a pH of 7.1 in a 4-liter three-necked flask by adding 1 g of borax. After 252 g of melamine have been added, a clear solution is obtained on warming to 75° C., while stirring with a hook stirrer. Methylolation is then carried out at 75° C. for 2 hours, a readily stirrable slurry being formed. After 1,600 g of methanol have been added, the contents of the flask are cooled to 40° C. in the course of one hour and 27 g of 55% strength nitric acid are added for the etherification. The clear solution formed after etherifying for approx. 2 hours is processed further as described in Example 1.

The resulting 95% strength methyl-etherified methylolmelamine, has a viscosity of 3.9 Pa.s at 25° C. and contains approx. 5.7 mols of formaldehyde and approx. 4.7 mols of methyl-etherified methylol groups, per mol of melamine.

EXAMPLE 4

Melamine:formaldehyde:methanol molar ratio = 1:8:25

1,231 g of a 39% strength aqueous solution of formaldehyde (pH 3.7) are adjusted to pH 7 in a 4-liter three-necked flask by adding 1 g of borax. After 252 g of melamine have been added, the contents of the flask are stirred for 2 hours at 75° C., as described in Example 3, and are then etherified and worked up as described in that example. The resulting 95% strength methyl-etherified methylolmelamine, has a viscosity of 5.6 Pa.s at 25° C. and contains approx. 5.9 mols of formaldehyde and approx. 4.6 mols of methyl-etherified methylol groups, per mol of melamine.

EXAMPLE 5

Melamine:formaldehyde:methanol molar ratio = 1:7.4:25

1,139 g of a 39% strength aqueous solution of formaldehyde (pH 3.5) are adjusted to pH 6.9 in a 4-liter three-necked flask by adding 0.6 g of borax. After 252 parts by weight of melamine have been added, the contents of the flask are warmed to 75° C., while stirring with a hook stirrer, a clear solution being formed. After methylolation at 75° C. for 2½ hours, 1,600 g of methanol are added to the contents of the flask and further processing is carried out as in Example 1.

The resulting 95% strength methyl-etherified methylolmelamine, has a viscosity of 9.5 Pa.s at 25° C. and contains approx. 5.6 mols of formaldehyde and approx. 4.5 mols of methyl-etherified methylol groups, per mol of melamine.

EXAMPLE 6

Melamine:formaldehyde:methanol molar ratio = 1:7.4:25

1,139 g of a 39% strength aqueous solution of formaldehyde (pH 3.9), containing 80 g of methanol as a stabiliser, are adjusted to pH 7.2 in a 4-liter three-necked flask by adding 1.1 g of borax. After 252 g of melamine have been added, the contents of the flask are warmed to 75° C., while stirring with a hook stirrer, a clear solution being formed. Methylolation at 75° C. for 2½ hours gives a readily stirrable slurry, which is processed further, as described in Example 1, after 1,520 g of methanol have been added.

The end product obtained is a 95% strength methyl-etherified methylolmelamine, which has a viscosity of 8.3 Pa.s at 25° C. and contains approx. 5.8 mols of formaldehyde and approx. 4.7 mols of methyl-etherified methylol groups, per mol of melamine.

EXAMPLE 7

Melamine:formaldehyde:methanol molar ratio = 1:7.4:25

987 g of a 45% strength aqueous solution of formaldehyde (pH 3.5) are adjusted to pH 7.1 in a 4-liter three-necked flask by adding 1 g of borax. After 252 g of melamine have been added, warming to 75° C., while stirring with a hook stirrer, gives a clear solution at first and, after methylolation at 75° C. for 2 hours, a readily stirrable slurry of the methylolmelamine, which is processed further, as described in Example 1, after 1,600 g of methanol have been added.

The resulting 95% strength methyl-etherified methylolmelamine, has a viscosity of 2.3 Pa.s at 25° C. and contains approx. 5.9 mols of formaldehyde and approx. 4.9 mols of methyl-etherified methylol groups, per mol of melamine.

EXAMPLE 8

Melamine:formaldehyde:methanol molar ratio = 1:7.4:25

1,269 g of a 35% strength aqueous solution of formaldehyde (pH 3.7) are adjusted to pH 7.3 in a 4-liter three-necked flask by adding 1.8 g of borax. After 252 g of melamine have been added, methylolation is carried out at 75° C. for 2 hours, while stirring with a hook stirrer.

The readily stirrable slurry of methylolmelamine obtained is processed further, as described in Example 1, after 1,600 g of methanol have been added.

The end product obtained is a 95% strength methyl-etherified methylolmelamine, which has a viscosity of 7.7 Pa.s at 25° C. and contains approx. 5.7 mols of formaldehyde and approx. 4.5 mols of methyl-etherified methylol groups, per mol of melamine.

EXAMPLE 9

Melamine:formaldehyde:methanol molar ratio = 1:7.4:21

1,139 g of a 39% strength aqueous solution of formaldehyde (pH 3.1) are adjusted to pH 6.7 in a 4-liter three-necked flask by adding 1 g of borax. After 252 g of melamine have been added, the contents of the flask are warmed to 75° C., while stirring with a hook stirrer, a clear solution being formed. After methylolation at 75° C. for 2 hours, 1,344 g of methanol are added to the contents of the flask and further processing is carried out, as described in Example 1.

The resulting 95% strength methyl-etherified methylolmelamine, has a viscosity of 9.6 Pa.s at 25° C. and contains approx. 5.8 mols of formaldehyde and approx. 4.6 mols of methyl-etherified methylol group, per mol of melamine.

Unless otherwise specified in the preceding examples, the methanol content of the formaldehyde solutions used was less than 1% by weight.

We claim:

1. The process for manufacture of methanol-etherified methylolmelamines which are largely monomeric containing more than 5 mols of formaldehyde and more than 4 mols of methyl-etherified methylol groups, per mol of melamine, and having a viscosity of less than 20 pascal-seconds at 25° C. and a solids content of at least 95%, comprising (a) methylolating melamine with formaldehyde at a molar melamine:formaldehyde ratio of 1:6.5 to 1:8 for 1½ to 5 hours at 50° C. to 85° C., with the formaldehyde source being an aqueous solution of formalin containing 30 to 50% by weight of formaldehyde and having a pH of 6.7 to 7.3, and (b) etherifying the resulting suspension of methylolmelamine with 15 to 30 mols of methanol per mol of melamine at temperatures of 30° C. to 60° C. in the presence of a strong acid.

2. The process according to claim 1 wherein the molar ratio of melamine and formaldehyde is 1:7 to 1:7.5.

3. The process according to claim 1 borax is added to the formalin solution to adjust the pH to 6.7–7.3.

4. The process according to claim 1 wherein the methylolation temperature is 65° C. to 75° C.

5. The process according to claim 1 wherein melamine is methylolated for a period of 2 to 3 hours.

6. The process according to claim 1 wherein the etherification temperature is 35° C. to 45° C.

7. The process according to claim 1 wherein said strong acid is nitric acid, sulphuric acid, hydrochloric acid, phosphoric acid, trichloroacetic acid, p-toluenesulphonic acid, or mixtures thereof.

8. The process according to claim 1 wherein said strong acid is nitric acid.

9. The process according to claim 1 wherein the suspension of methylolmelamine obtained in the methylolation reaction (a) is etherified in the same vessel without isolating and without intermediately drying the methylolmelamine.

10. The process according to claim 1 wherein after the completion of (a), methanol is added, the mixture is cooled to 30° C. to 60° C. and the methylolmelamine is etherified.

* * * * *